United States Patent [19]

Simpson et al.

[11] Patent Number: 5,002,066
[45] Date of Patent: Mar. 26, 1991

[54] BLOOD SAMPLING APPARATUS

[75] Inventors: Shawn L. Simpson, Toledo, Ohio; Steven E. Young, Temperance, Mich.; David G. Musgrove, Worthington, Ohio

[73] Assignee: Medex, Inc., Hilliard, Ohio

[21] Appl. No.: 288,568

[22] Filed: Dec. 22, 1988

[51] Int. Cl.$^5$ .............................................. A61B 5/00
[52] U.S. Cl. ........................................ 128/760; 604/52
[58] Field of Search ............... 128/672, 673, 675, 760, 128/763, 765, 770; 604/51–53, 93, 181, 187, 188, 264, 272

[56] References Cited

U.S. PATENT DOCUMENTS

| | | | |
|---|---|---|---|
| 3,157,201 | 11/1964 | Littmann | 128/675 |
| 3,340,869 | 9/1967 | Bane | 128/765 |
| 4,431,009 | 2/1984 | Marino et al. | 128/675 |
| 4,447,235 | 5/1984 | Clarke | 128/760 |
| 4,610,256 | 9/1986 | Wallace | 128/675 |

FOREIGN PATENT DOCUMENTS

| | | | |
|---|---|---|---|
| 8801846 | 3/1988 | PCT Int'l Appl. | 128/673 |
| 2143803 | 2/1985 | United Kingdom | 128/760 |

*Primary Examiner*—Max Hindenburg
*Attorney, Agent, or Firm*—Wood, Herron & Evans

[57] ABSTRACT

In blood pressure monitoring apparatus, apparatus for withdrawing blood from a tube connected to a patient's blood vessel. A stopcock is connected to the tube. A T-connector is connected to one port of the stopcock. A storage syringe is connected to one branch of the T-connector and a latex self-sealing cap covers the other port to provide an IV site suitable for penetration with a syringe needle to withdraw a blood sample through the IV site. The storage syringe brings blood to the T-connector so that it can be withdrawn through the IV site.

7 Claims, 1 Drawing Sheet

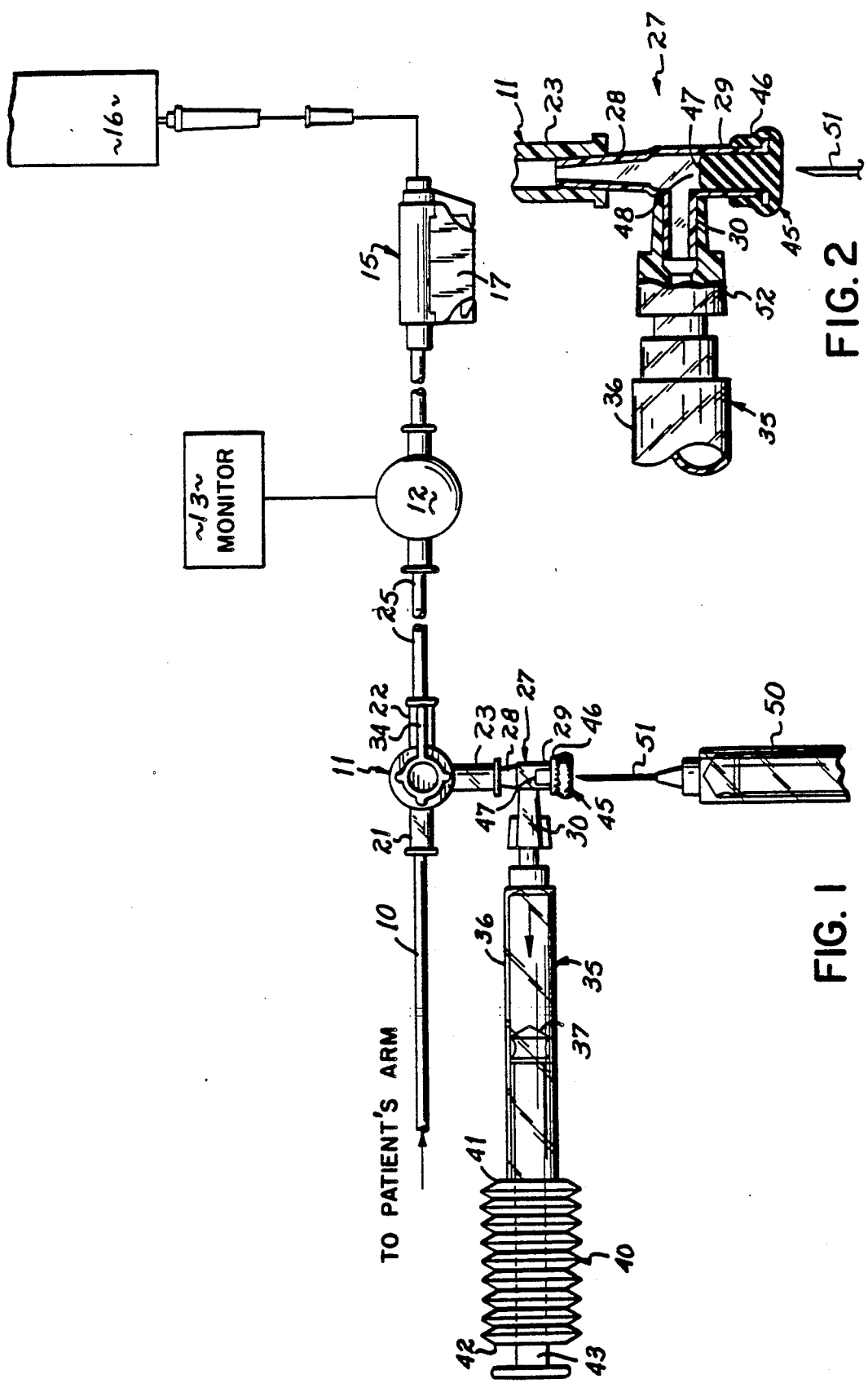

BLOOD SAMPLING APPARATUS

This invention relates to blood pressure monitoring apparatus, and particularly the invention relates to apparatus for removing samples of a patient's blood during a blood pressure monitoring procedure.

BACKGROUND OF THE INVENTION

Blood pressure monitoring apparatus is well known. It includes a catheter inserted into a patient's blood vessel, a tube connecting the catheter to a transducer, a supply of saline solution connected through the transducer to the catheter and a flush valve connected in the line to the catheter. The system through the catheter is filled with the saline solution, the saline solution forming a static column between the patient's blood vessel and the transducer whereby variations in blood pressure are communicated to the transducer so that the patient's blood pressure is monitored in real time. The flush valve has a capillary through which the saline solution flows, very slowly, to the patient. The slow dripping of the saline solution prevents any clotting of blood in the catheter which might introduce an error into the monitoring of the blood pressure. The flush valve contains a bypass by which a rapid flow of saline solution can be introduced into the system as needed.

It has been conventional to provide a site for withdrawing a blood sample. A stopcock is placed in series between the catheter and the transducer. The stopcock has a port that is normally closed by a solid plug (dead ender), the port being covered by a dust cover. The procedure for drawing a blood sample through the free port on the stopcock has required the following major steps: The stopcock is shifted to block flow of saline solution from the supply and open ports between the catheter and the plugged port. The dust cover is removed and the dead ender plug is moved and carefully set aside to avoid contamination. A syringe is inserted in the opening created by the removal of the dead ender and about 2 cc mixture of blood and saline is withdrawn to remove the saline from the catheter and tube leading to the stopcock so that only blood is present at the free port of the stopcock. A heparinized syringe is inserted into the free stopcock port to withdraw about 1 cc of blood. The stopcock is shifted to open the free port to the saline supply and block the port to the catheter. The free port is flushed, using the flush valve, with saline and the dead ender is replaced. The stopcock is then shifted again to block the free port and connect the catheter to the saline supply. The flush valve then flushes the blood out of the tube and catheter, whereupon the system between the catheter and transducer is filled and ready for resumption of normal monitoring operation.

The foregoing procedure has obvious disadvantages. A number of manipulative steps are required to obtain the blood sample. A number of chances for contamination of the patient's blood are presented in the opening of the port to bring the blood to the stopcock for sampling. Blood usually drips from the sampling port. The exposure of attending people to the patient's blood is a matter of considerable concern because of the possibility of spreading AIDS, hepatitis and the like.

BRIEF SUMMARY OF THE INVENTION

The objective of the present invention has been to provide a simpler system for taking samples of blood from the blood pressure monitoring apparatus wherein the chance for contaminating the patient is substantially entirely eliminated and the possibility of blood inadvertently contaminating the area around the patient is also eliminated.

The objective of the present invention is achieved by mounting a T-connector on the free port of the blood sampling stopcock. The T-connector provides two available branches. A storage syringe is mounted to one of the branches and an IV site is formed at the other of the branches.

The blood sampling operation, with the apparatus of the present invention, is greatly simplified. With the stopcock positioned to connect the T-connector to the patient and block the supply of saline, the storage syringe withdraws the approximately 2 cc of solution from the catheter tubing and stopcock to bring the patient's blood to the intersection of the T-connector. A sampling syringe is then introduced through the IV site to withdraw a 1 cc sample. After the sample has been withdrawn, the storage syringe expels the saline solution back through the circuit to the patient. The stopcock is shifted and the flush valve manipulated to clean the system of any residual blood from the sampling process.

From the foregoing, it can be seen that the manipulative steps are greatly reduced by the present invention. The system is never opened to atmosphere so that contaminants cannot be introduced through the free port. There is no possibility of blood from the patient escaping the system to contaminate the area around the patient.

Another one of the features of the invention has been to provide a flexible bellows-shaped sleeve between the cylinder of the storage syringe and its plunger so that when the plunger is withdrawn to draw saline into the storage syringe, no contaminants from the atmosphere can contact the plunger and inadvertently get into the system.

Further, the IV site is covered by a latex cap having a central plug that projects up to the intersection of the T-connector to provide assurance that when the saline solution is brought into the storage syringe, the blood will be immediately adjacent the latex cap and accessible to the sampling syringe.

BRIEF DESCRIPTION OF THE DRAWINGS

The several features of the invention will become more readily apparent from the following detailed description taken in conjunction with the accompanying drawings in which:

FIG. 1 is a diagrammatic elevational view of the blood pressure monitoring apparatus; and FIG. 2 is an enlarged view, partly in section, of the invention of the apparatus.

DETAILED DESCRIPTION OF THE DRAWINGS

Referring to FIG. 1, a tube 10 is connected via a catheter to the patient's arm. The tube 10 is connected by way of a blood sampling stopcock 11 to a blood pressure transducer 12. The blood pressure transducer can be a disposable or reusable transducer such as are well known in the art. The transducer is connected to a monitor 13 by which variations in blood pressure can be viewed and recorded. The blood pressure transducer is connected to a flush valve 15. The flush valve is connected to a supply of saline solution 16. The flush valve has a marine capillary tube in series between the saline supply 16 and transducer 12 to assure a continued slow dripping of saline solution through the system to the catheter. A large bypass passageway is provided in the flush valve in parallel with the capillary tube. That large passageway is normally closed and is opened by squeezing the operators 17 to greatly increase the flow of saline solution to the system. Thus far described, the apparatus is conventional and has been in use in hospitals for many years.

The stopcock 11 has three ports 21, 22 and 23. The first port 21 is connected to the tube 10 leading to the catheter. The second port 22 is connected to a tube 25 that leads to the transducer 12. A T-connector 27 has three branches 28, 29, and 30. One of the branches, 28, is connected to the third stopcock port 23.

Internally, the stopcock 11 has a valve rotatable by a handle 34 that can block the flow through any of the three ports 21, 22, 23. Normally, the projecting handle 34 points to the "off" position, that is, the blocked port. Thus, in the illustrated position of the stopcock, the port 22 is blocked while flow from the ports 21 and 23 is open.

A storage syringe 35 is mounted on the branch 30 of the T-connector 27. The storage syringe has a barrel 36 and a plunger 37. A bellows-shaped flexible sleeve 40 has one end 41 connected to the barrel 36. The other end of the sleeve 42 is connected to the free end 43 of the plunger 37. It can be seen that the sleeve keeps the plunger free from exposure from contaminants when the plunger is withdrawn to fill the barrel 36.

The branch 29 is closed by a self-sealing latex cap 45. As best shown in FIG. 2, the cap 45 has a skirt 46 surrounding the branch 29 of the T-connector 27. A central plug 47 extends through the branch 29 to the intersection 48 of the T-connector.

A syringe 50 having a needle 51 can penetrate the self-sealing cap 45 to bring the needle into the intersection 48 of T-connector 27 for the purpose of withdrawing a sample.

The T-connector 27 has its branch 28 fixed to the port 23 as by means of a solvent. The storage syringe 35 may be connected to the T-connector in any fashion and may include a conventional Luer lock indicated at 52.

In the operation of the invention, the stopcock 11 has its handle 34 normally overlying the port 23 so as to open the ports 21 and 22 to permit a communication between the patient's blood vessel and the transducer and to permit flow of saline solution from the supply 16 to the end of the catheter via the flush valve.

When a blood sample is to be taken, a procedure that may be performed many times during a day, the stopcock handle 34 is turned to the illustrated position blocking port 22. At this time, the tube 10 and stopcock are filled with saline solution. The plunger 37 of the storage syringe 35 is withdrawn to fill the barrel 36 with saline solution from the tube 10 until blood from the patient runs through the stopcock and into the connector 27. When the blood has presented itself in the connector 27, the syringe 50 is inserted through the self-sealing cap 45 into the intersection 48. There, blood, substantially free of saline solution, is withdrawn. The sampling syringe 50 is then removed. The plunger 37 of the storage syringe is returned to its former position in the barrel 36 to expel the saline solution and blood back through the T-connector 27, stopcock 11, tube 10 into the patient's arm. The stopcock handle 34 is then returned to the position overlying port 23. The flush valve 15 may be briefly manipulated to permit fresh saline solution to flow through the bypass passageway to clean any residual blood from the tube 10.

From the above disclosure of the general principles of the present invention and the preceding detailed description of a preferred embodiment, those skilled in the art will readily comprehend the various modifications to which the present invention is susceptible. Therefore, we desire to be limited only by the scope of the following claims and equivalents thereof:

We claim:

1. Apparatus for withdrawing blood from a tube connected to a patient's blood vessel comprising:
   a tube connectable between a patient's blood vessel and a saline supply;
   a branch line intersecting said tube and connected to said tube out of the normal path between said saline supply and said blood vessel, said branch line having two ports,
   a storage syringe permanently connected to one of said ports,
   the other of said ports forming an IV site for temporary receipt of a sampling syringe,
   a self-sealing cap covering said other port,
   whereby said storage syringe can temporarily remove saline solution from said tube and bring blood to said IV site, a sampling syringe can withdraw blood from said IV site and thereafter the storage syringe can return the removed solution to the tube.

2. Apparatus as in claim 1 in which said storage syringe has a barrel and a plunger slidable in said barrel, and means for preventing contamination of said plunger and the interior of said barrel.

3. Apparatus as in claim 1 further comprising,
   a self-sealing latex cap covering said IV site.

4. Apparatus as in claim 1 in which a T-connector having three ports is connected at one port to said branch line, the second of said ports being connected to said storage syringe, and a third port forming said IV site,
   and a self-sealing latex cap covering said third port, said cap having a plug extending to said second port so that when blood is brought to said second port by said storage syringe, the blood will be adjacent the end of said plug in position for sampling.

5. Apparatus for withdrawing blood from a tube connected to a patient's blood vessel, said tube also being connected to a saline solution supply, said apparatus comprising:
   a stopcock having first, second and third ports, said first port adapted to be connected to said tube, said second port adapted to be connected to said saline solution supply,
   a T-connector having three branches, a first branch connected to said third port,
   a storage syringe permanently connected to a second branch,
   a self-sealing latex cap forming an IV site connected to said third branch for temporary receipt of a sampling syringe,
   said stopcock having means for selectively closing one port while the remaining ports are open,
   whereby said stopcock can be operated to close the port to said saline solution supply and open the remaining ports, the storage syringe can be operated to withdraw saline solution from said tube and bring blood into said T-connector, the sampling syringe can be inserted in said IV site to withdraw blood, and said storage syringe can be operated to return blood to the patient and saline solution to said tube.

6. Apparatus for withdrawing blood from a tube connected to a patient's blood vessel comprising:
   a tube connectable to a patient'blood vessel,
   a branch line connected to said tube, said branch line having two ports,
   a storage syringe connected to one of said ports,
   the other of said ports forming an IV site for temporary receipt of a sampling syringe,
   a self-sealing cap covering said other port,
   whereby said storage syringe can temporarily remove saline solution from said tube and bring blood to said IV site, whereupon a sampling syringe can withdraw blood from said IV site,
   said storage syringe having a barrel and a plunger slidable in said barrel and having an end projecting from said barrel,
   and a flexible sleeve connected at one end to said barrel and connected at the other end to the projecting end of said plunger.

7. Apparatus for withdrawing blood from a tube connected to a patient'blood vessel, said tube also being connected to a saline solution supply, said apparatus comprising:

a stopcock having first, second and third ports, said first port adapted to be connected to said tube, said second port adapted to be connected to said saline solution supply,
a T-connector having three branches, a first branch connected to said third port,
a storage syringe connected to a second branch,
a self-sealing latex cap forming an IV site connected to said third branch for temporary receipt of a sampling syringe,
said stopcock having means for selectively closing one port while the remaining ports are open,
whereby said stopcock can e operated to close the port to said saline solution supply and open the remaining ports, the storage syringe can be operated to withdraw saline solution from said tube and bring blood into said T-connector, the sampling syringe can be inserted in said IV site to withdraw blood, and said storage syringe can be operated to return blood to the patient and saline solution to said tube,
said storage syringe having a barrel and a plunger within said barrel,
and a flexible sleeve connected between said barrel and plunger to keep contaminants out of said storage syringe.

* * * * *